(12) United States Patent
Tayebi

(10) Patent No.: US 8,334,008 B1
(45) Date of Patent: Dec. 18, 2012

(54) ARTICLE FOR DISPENSING A MEDICINAL INGREDIENT AND A METHOD THE MANUFACTURE THEREOF

(76) Inventor: Amad Tayebi, Westford, MA (US)

( * ) Notice: Subject to any disclaimer, the term of this patent is extended or adjusted under 35 U.S.C. 154(b) by 1200 days.

(21) Appl. No.: 12/156,890

(22) Filed: Jun. 5, 2008

Related U.S. Application Data

(60) Provisional application No. 60/933,200, filed on Jun. 5, 2007.

(51) Int. Cl.
*A61L 33/06* (2006.01)
(52) U.S. Cl. ............ 427/2.24; 427/293; 427/385.5; 604/289; 604/290; 604/294; 604/891.1

(58) Field of Classification Search ............ 427/2.24
See application file for complete search history.

(56) References Cited

U.S. PATENT DOCUMENTS

| | | | | |
|---|---|---|---|---|
| 2005/0095269 | A1* | 5/2005 | Ainpour et al. | 424/427 |
| 2007/0233037 | A1* | 10/2007 | Gifford, et al. | 604/521 |
| 2007/0298075 | A1* | 12/2007 | Borgia et al. | 424/428 |

* cited by examiner

*Primary Examiner* — John J Figueroa
(74) *Attorney, Agent, or Firm* — American Patent Associates; Amad Tayebi

(57) ABSTRACT

A method is provided for making punctal plugs by providing a fibrous strand and extrusion or dip coating the fibrous strand with a polymeric coating and cutting the coated fibrous strand to adequate length for insertion into a mammal body conduit, vessel, cavity, canal, artery, or vein.

3 Claims, 6 Drawing Sheets

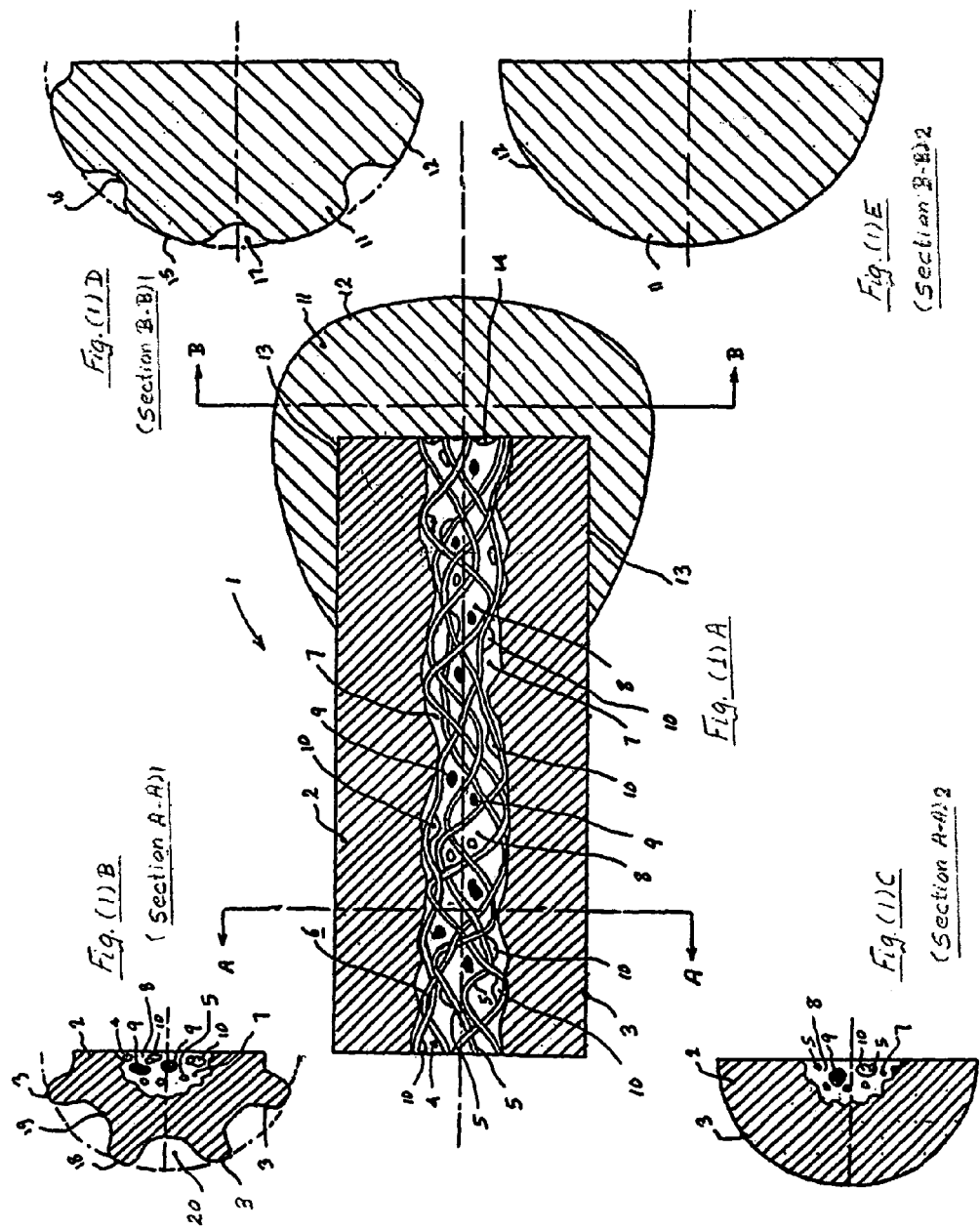

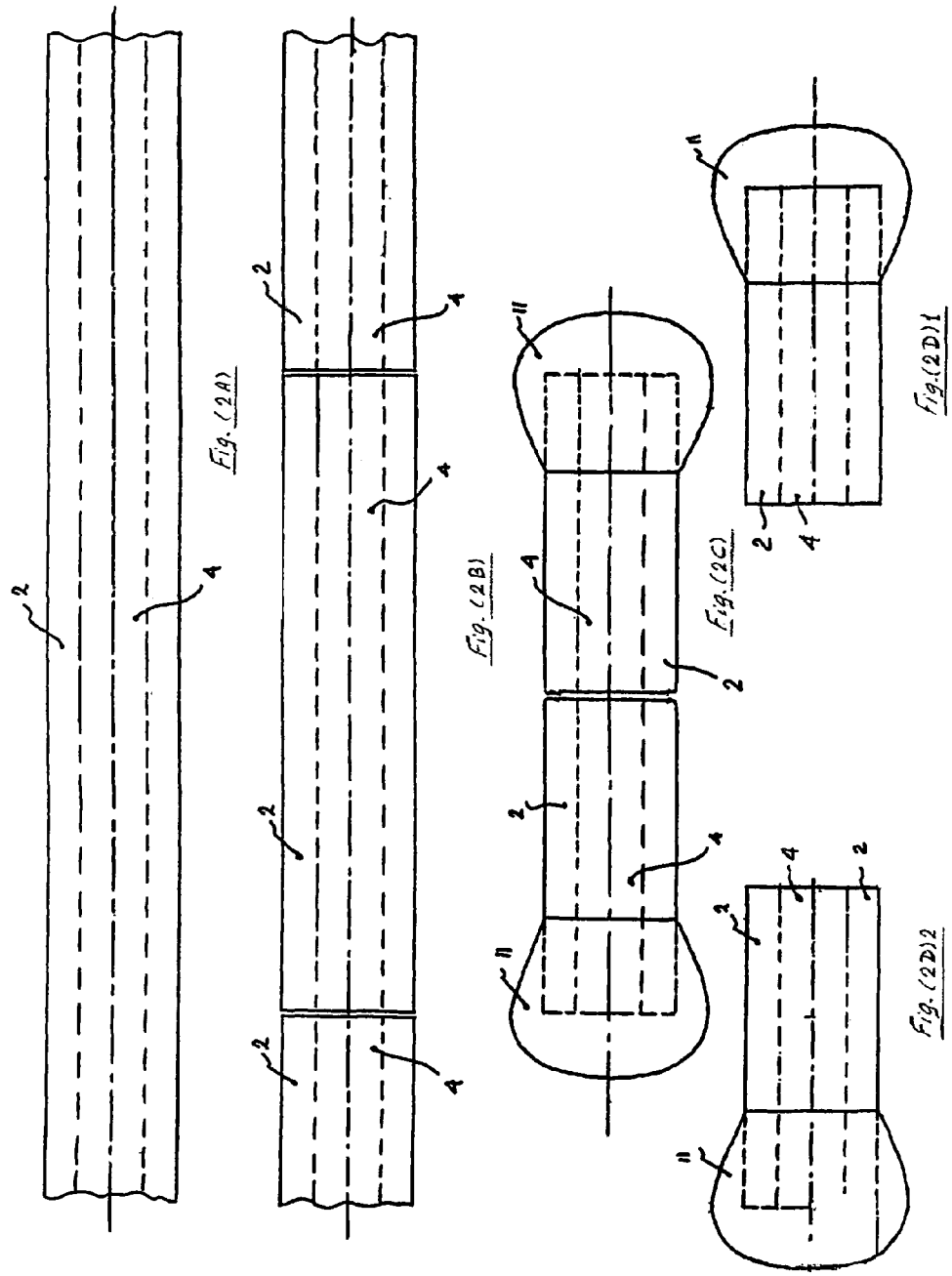

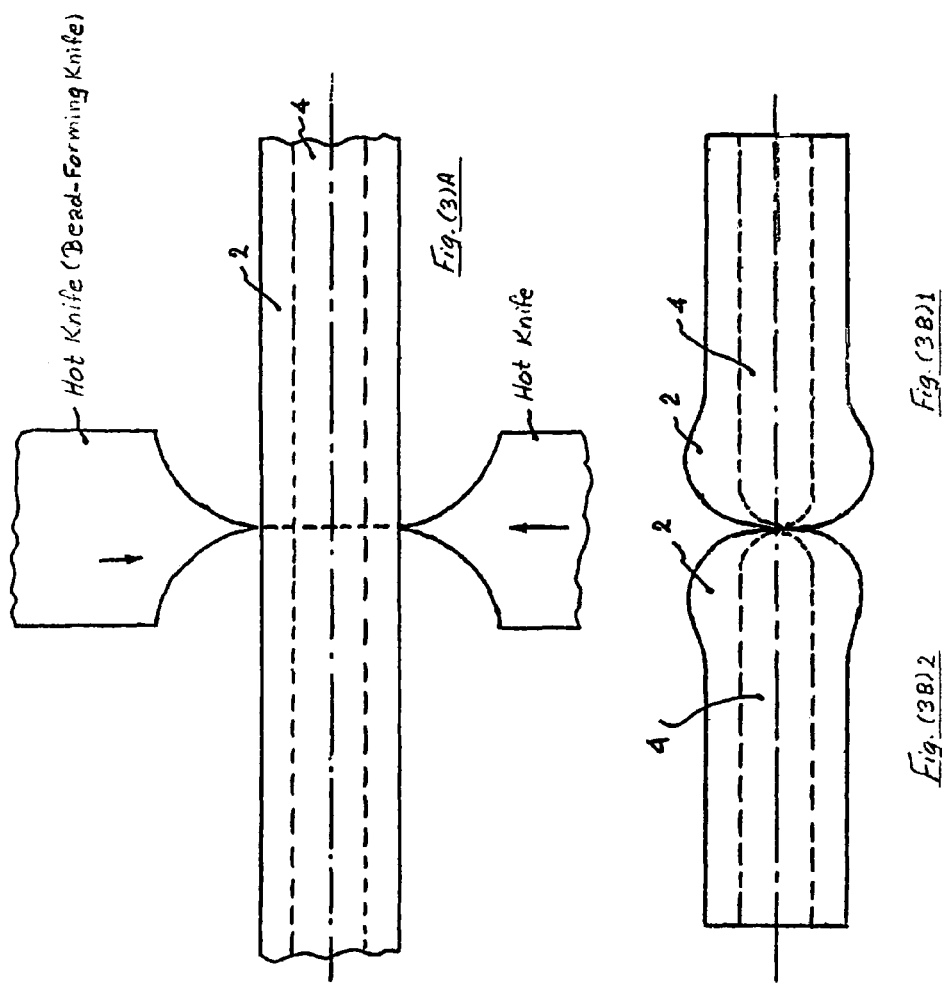

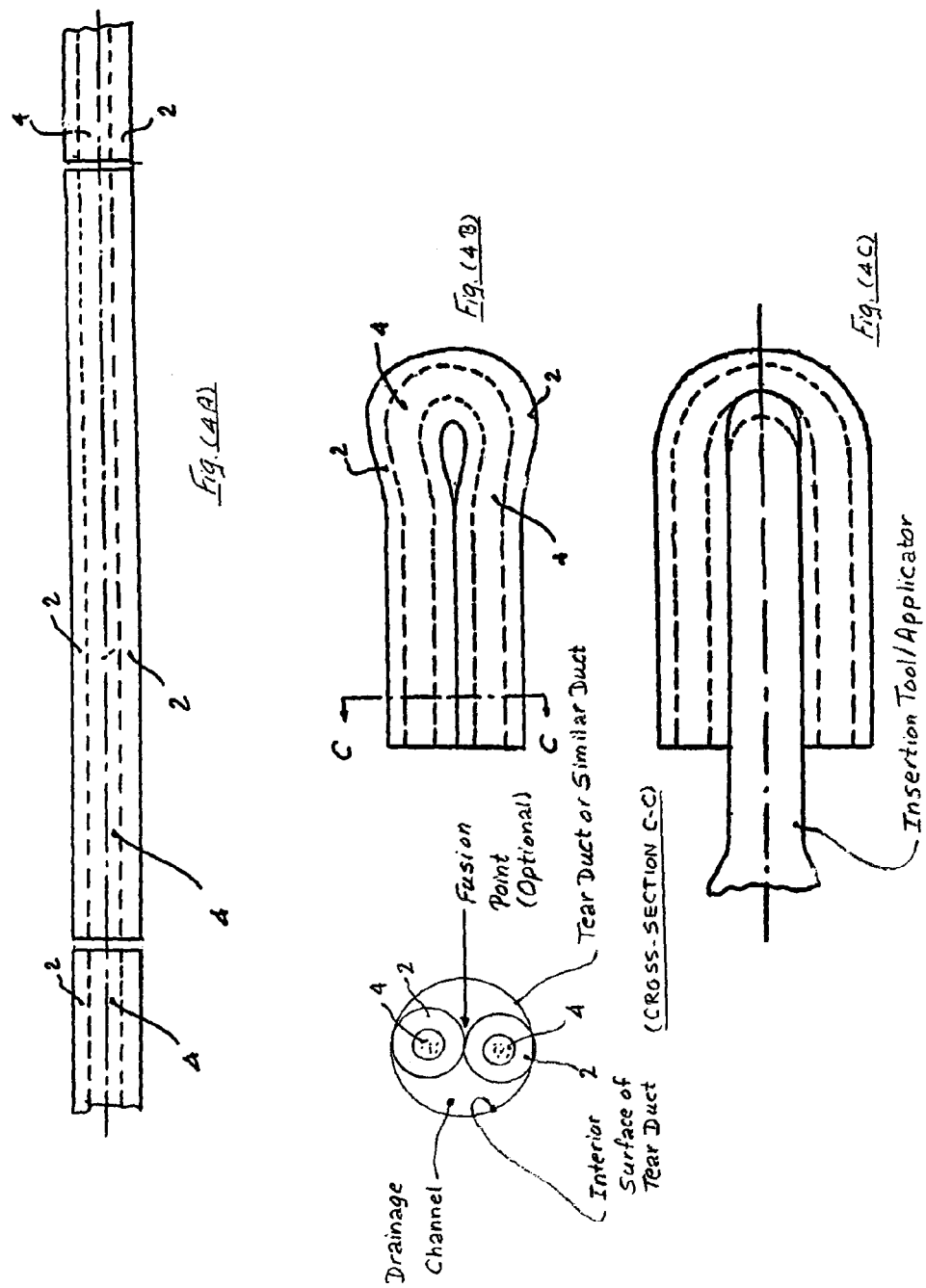

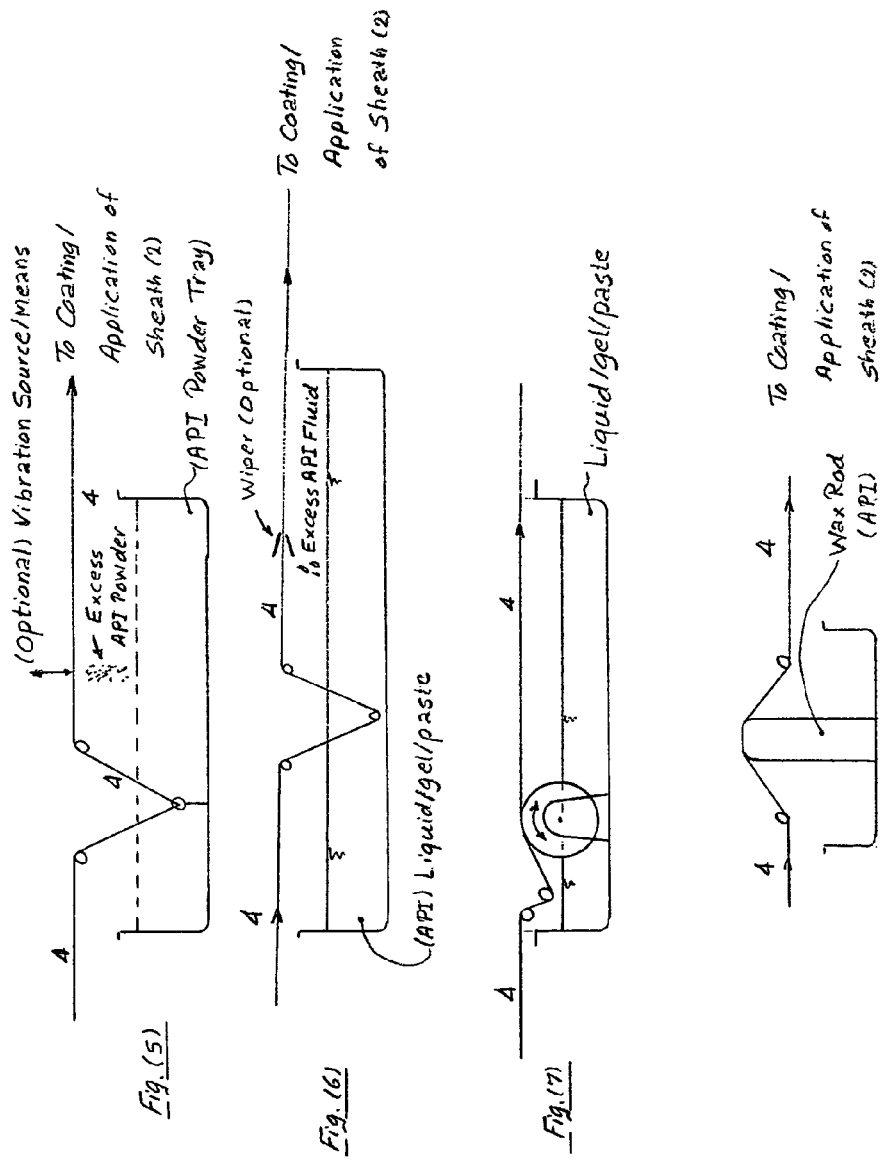

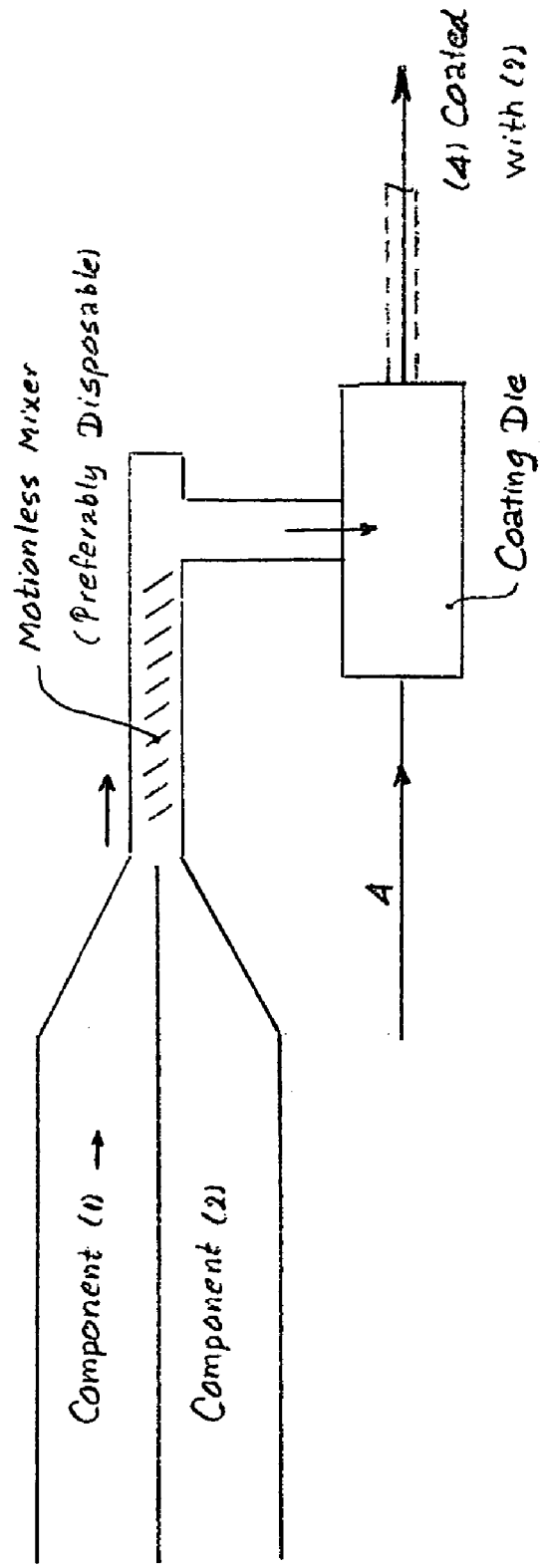
Fig. (9)

ARTICLE FOR DISPENSING A MEDICINAL INGREDIENT AND A METHOD THE MANUFACTURE THEREOF

PRIORITY CLAIM

This application claims priority from Provisional Patent Application Ser. No. 60/933,200 filed on Jun. 5, 2007.

FIELD OF THE INVENTION

The present invention is in the field of articles for dispensing medicinal ingredients by insertion of the articles into a mammal body conduit, vessel, cavity, canal, artery, or vein and allowing interaction between bodily fluid(s) and medicinal ingredient(s) contained in the articles. More particularly, the present invention provides a method of making punctal plugs for delivery of medicinal ingredients to the eye, throat or nose of humans.

BACKGROUND OF THE INVENTION AND RELATED PRIOR ART

Examination of the prior art reveals a large number of patents and pending patent applications that address the subject matter of the present invention, including chemical composition of materials that may be used in making and/or compounding the material of the medicine dispensing articles, active medicinal ingredients that may be incorporated into the medicine dispensing articles, functional aspects and structure, design and geometric configurations of the medicine dispensing articles, for example, U.S. Pat. Nos. 3,949,750, 5,171,270, 5,283,063, 5,437,625, 5,469,867, 5,593,393, 5,723,005, 5,817,335, 5,962,548, 6,020,445, 6,099,852, 6,234,175, 6,238,363, 6,306,114, 6,367,929, 6,428,502, 6,679,605, 6,822,016, and 6,923,800 and U.S. Pending Application No. US 20050095269, 20050197614, 20050232972, 20060106352, 20060172972, 20070298075, 20070299516, 20080045911, and 20080114076. Each of these listed Patents and Pending Patent Applications and their respective teachings are incorporated in the present invention, in their respective entireties, by reference.

DESCRIPTION OF THE INVENTION

Referring to FIGS. 1 to 9, the numbers used in the drawings to identify elements, components or locations shown in the drawings are described as follows:
1: Article for dispensing medicinal ingredients
2: Exterior Sheath of 1 or body of punctal plug
3: Exterior surface of 2
4: Fibrous Core (multifilament strand). Strand may be in the form of a multifilament yarn or tow made of continuous or discontinuous fibers and/or filaments. Strand may be twisted or untwisted. Strand may be needled or un-needled. Fibers/Filaments may be bio-absorbable or may comprise bio-absorbable fibers, segments or portions. Strand may be in the form of a braid (circular or flat). The braid may have core element(s) or may have no core element. Fibers comprising the strand may have straight segments and crimped segments. Fibers comprising the strand have inter-fiber spacings (8) and high capillary action inter-fiber contact points (6). Core elements of braid-type strand may be straight fibers and/or crimped fibers. Alternatively, fibrous core 4 may be in the form of a monofilament impregnated with an A.P.I. (Active Pharmaceutical Ingredient).
5: Fibers comprising fibrous core 4.
6: High capillary action inter-fiber contact points.
7: Spacings between interior surface of exterior sheath 2 and fibers of fibrous core 4.
8: Inter-fiber spacings.
9: Medicinal ingredient (Active Pharmaceutical Ingredient API) in powder/particulate form.
10: Active Pharmaceutical Ingredient, (API) in liquid, wax, gel or paste form.
11: End sealing bead.
12: Exterior surface of end sealing bead 11.
13: Bonding surface between end sealing bead 11 and exterior surface 3 of exterior sheath or body of punctal plug 2.
14: Interior surface of end sealing bead 11 facing cross-section of fibrous core 4.
15: Peaks of exterior surface 12 of end sealing bead 11 for the case when end sealing bead 11 is, optionally, embossed.
16: Valleys of exterior surface 12 of end sealing bead 11 for the case when end sealing bead 11 is, optionally, embossed.
17: Drainage channels formed/created between the interior surface of tear duct(s) and the exterior surface 12 of end sealing bead 11.
18: Peaks of exterior surface (3) of exterior sheath or body of punctal plug 2 of article 1, for the case when the exterior sheath or body of punctal plug 2 is, optionally, having a corrugated surface.
19: Valleys of exterior surface (3) of exterior sheath or body of punctal plug 2 of article 1, for the case when the exterior sheath or body of punctal plug 2 is, optionally, having a corrugated surface.
20: Drainage channels formed/created between the interior surface of tear ducts and exterior surface (3) of exterior sheath or body of punctal plug 2 of article 1.

Also, referring to FIGS. 1 to 9, the following is a Brief Description of the Drawings:

FIG. (1)A is a Front Cross-Sectional View of Article 1 for dispensing medicinal ingredients.

FIG. (1)B shows one half of (Section A-A) of Article 1 for dispensing medicinal ingredients.

FIG. (1)C shows one half of another alternative of (Section A-A) of Article 1 for dispensing medicinal ingredients.

FIG. (1)D shows one half of (Section B-B) of Article 1 for dispensing medicinal ingredients.

FIG. (1)E shows one half of another alternative of (Section B-B) of Article 1 for dispensing medicinal ingredients.

FIG. (2A) shows a longitudinal view of exterior sheath 2 of article 1 or body of punctal plug and fibrous core 4.

FIG. (2B) shows a longitudinal view of exterior sheath 2 of article 1 or body of punctal plug and fibrous core 4 cut into separate segments.

FIGS. (2C), (2D)1 and (2D)2 show longitudinal views of assemblies comprising exterior sheath 2 of article 1 or body of punctal plug, fibrous core 4 and end sealing bead 11.

FIG. (3)A shows a longitudinal view of exterior sheath 2 of article 1 or body of punctal plug and fibrous core 4 and hot bead-forming knives prior to cutting exterior sheath 2 and fibrous core 4.

FIGS. (3B)1 and (3B)2 show a longitudinal view of exterior sheath 2 of article 1 or body of punctal plug and fibrous core 4 after being cut by hot bead-forming knives.

FIG. (4A) shows a longitudinal view of exterior sheath 2 of article 1 or body of punctal plug and fibrous core 4 cut into separate segments prior to being folded as shown in FIG. 4B).

FIG. (4B) shows a longitudinal view of a segment of exterior sheath 2 of article 1 or body of punctal plug and fibrous core 4 after being folded, as shown, and a cross-sectional view C-C showing folded segment surrounded by tear duct or similar duct and drainage channel.

FIG. (4)C shows insertion tool/applicator.

FIG. 5 shows fibrous core 4 being guided through an API (Active Pharmaceutical Ingredient) powder tray then being directed to coating/application of sheath 2.

FIG. 6 shows fibrous core 4 being guided through an API (Active Pharmaceutical Ingredient) liquid/gel/paste then being directed to coating/application of sheath 2.

FIG. 7 shows fibrous core 4 being guided over a roll placed in a liquid/gel/paste tray.

FIG. 8 shows fibrous core 4 being guided over an API wax rod then being directed to coating/application of sheath 2.

FIG. 9 shows two components (component (1) and component (2)) directed into a motionless mixer then into a coating die in which fibrous core 4 is fed in and exits coated with sheath 2.

BRIEF SUMMARY OF THE INVENTION

The present invention provides a method of making a punctal plug. The method comprises the steps of providing a multi-filament strand, impregnating said multi-filament strand with an active pharmaceutical ingredient, coating the exterior surface of said strand with a polymeric material, and cutting the coated strand to desired length which is suitable for insertion into a mammal body conduit, vessel, cavity, artery or vein.

DETAILED DESCRIPTION OF THE INVENTION

With reference to FIGS. 1 to 9, and the numbers used in the drawings to identify elements, components or locations shown in the drawings, the present invention discloses a method comprising the steps of:

a) providing a multifilament strand/fibrous core 4,
b) impregnating the multifilament strand with an active pharmaceutical ingredient (API),
c) coating the exterior surface of fibrous core 4 with an impermeable coating/exterior sheath 2, and
d) cutting coated fibrous core 4 to desired length (s) to suit targeted end use/method of manufacture.

The active pharmaceutical ingredient (API) may be in a powder/particulate form, in the form of a gel, a liquid or a paste or in the form of a wax, Also, coating the exterior surface of fibrous core 4 with an impermeable coating/exterior sheath 2 is at a temperature not exceeding the maximum temperature the active pharmaceutical ingredient (API) may sustain without adversely impacting its (the API's) medicinal and performance properties. Exterior sheath 2 is a soft (low modulus) biocompatible material. For example, Elvax R ethylene vinyl acetate (EVA) resin made by DuPont, Elvax 3175 LG, having a melting point of 69 C (156 F) or similar and biocompatible material.

The coating process may be accomplished i) by a thermoplastic polymeric material extrusion through a wire coating type die, or ii) by application of a self-curing single or multiple component resin, for example, Room Temperature Curing Liquid Silicone Rubber (LSR).

For maintaining a uniform coating around fibrous core 4 and ingredient 9 and/or 10, application of tension on fibrous core 4 and alignment of axis of fibrous core 4 to be along the axis of coating die are essential process control parameters.

The above described method may also include the steps of a) sealing at least one end of cut length of coated strand by i) application of a bead 11 at said at least one end (see FIG. 2) and, optionally, embossing bead 11, (see FIG. (1)D, or ii) by hot sealing cut points by using specially profiled heated knives (see FIG. 3) or b) folding cut length into a hair-pin form suitable for insertion into tear ducts or similar ducts (see FIG. 4).

The invention claimed is:

1. A method of making punctal plugs for insertion into a mammal eye, throat or nose, said method comprising the steps of:
   providing a multi-filament strand,
   impregnating said multi-filament strand with an active pharmaceutical ingredient, extrusion coating the exterior surface of said strand with an impermeable polymeric material,
   and
   cutting the coated strand to desired length suitable for insertion into said mammal eye, throat or nose.

2. The method of making punctual plugs in accordance with claim 1, further comprising the step of sealing at least one end of cut length of said coated strand.

3. A punctal plug made in accordance with claim 1.

* * * * *